United States Patent [19]
Ishibashi et al.

[11] 4,159,378
[45] Jun. 26, 1979

[54] METHOD FOR THE PREPARATION OF DERIVATIVES OF URACIL

[75] Inventors: Kenichi Ishibashi, Urawa; Susumu Ishiguro, Washimiya; Reiko Komaki, Kawaguchi, all of Japan

[73] Assignee: Toshin Chemical Co., Ltd., Tokyo, Japan

[21] Appl. No.: 884,525

[22] Filed: Mar. 8, 1978

[30] Foreign Application Priority Data

Sep. 19, 1977 [JP] Japan ............................ 52-112311
Dec. 14, 1977 [JP] Japan ............................ 52-150126

[51] Int. Cl.$^2$ ........................................... C07D 239/54
[52] U.S. Cl. ..................................... 544/313; 544/314
[58] Field of Search ............................. 544/314, 313

[56] References Cited

U.S. PATENT DOCUMENTS

| 3,635,946 | 1/1972 | Giller et al. | 536/23 |
| 4,039,546 | 8/1972 | Giller et al. | 544/314 |
| 4,121,037 | 10/1978 | Nakamura et al. | 544/313 |

*Primary Examiner*—Paul M. Coughlan, Jr.
*Attorney, Agent, or Firm*—Sprung, Felfe, Horn, Lynch & Kramer

[57] ABSTRACT

A novel and very elegant method is proposed for the preparation of $N_1$-(2-tetrahydrofuryl)-5-substituted or -unsubstituted uracil, especially, $N_1$-(2-tetrahydrofuryl)-5-fluorouracil, by the reaction of the corresponding 5-substituted uracil compound with 2,3-dihydrofuran. The reaction is performed in the presence of a chlorosilane compound, e.g. dimethyldichlorosilane, and a catalytic amount of an organic amine compound and can proceed very rapidly without disadvantageous side reactions to give the objective compound with high purity in a high yield.

12 Claims, No Drawings

METHOD FOR THE PREPARATION OF DERIVATIVES OF URACIL

BACKGROUND OF THE INVENTION

The present invention relates to a novel and improved method for the preparation of derivatives of uracil or, in particular, to a method for the preparation of $N_1$-(2-tetrahydrofuryl)uracil substituted or unsubstituted at the 5-position.

$N_1$-(2-Tetrahydrofuryl)-5-substituted uracil derivatives, for example, $N_1$-(2-tetrahydrofuryl)-5-fluorouracil, is a well known compound having therapeutic activity as an anti-tumor agent or an anti-leukaemia agent.

In the prior art, several methods are proposed for the synthetic preparation of $N_1$-(tetrahydrofuryl)uracil derivatives including (1) the reaction of 2,4-bis(trimethylsilyl)uracil, substituted or unsubstituted at the 5-position, with 2-chloro-, 2-acyloxy- or 2-alkoxytetrahydrofuran (see, for example, British Patent Specification No. 1,168,391, U.S. Pat. No. 3,912,734, Belgian Pat. No. 807,556 and Japanese Patent Publications Sho. No. 49-10510, Sho. No. 52-5517 and Sho. No. 52-5519), (2) the direct reaction of uracil, substituted or unsubstituted at the 5-position, with 2-chloro-, 2-acyloxy- or 2-alkoxytetrahydrofuran (see, for example, Japanese Patent Publication Sho. No. 52-5518 and Japanese Patent Disclosures Sho. No. 51-8282 and Sho. No. 51-52182), (3) the reaction of 2,4-bis(trialkylstannyl)uracil, substituted or unsubstituted at the 5-position, with 2-chloro-, 2-acyloxy- or 2-alkoxytetrahydrofuran (see, for example, German OLS No. 2,648,239 and Japanese Patent Disclosure Sho. No. 52-83473) and (4) the reaction of 2,4-bis(trimethylsilyl)uracil, substituted or unsubstituted at the 5-position, with 2,3-dihydrofuran (see, for example, Japanese Patent Disclosures Sho. No. 52-31079 and Sho. No. 52-59173, U.S. Pat. No. 4,039,546 and Belgian Pat. No. 830,215).

These prior art methods have, however, their own respective drawbacks. For example, the methods (1) and (4) with 2,4-bis (trimethylsilyl)-5-substituted uracil compounds as the starting material are quite disadvantageous industrially because the preparation of the starting material requires an extremely high temperature of 140° to 170° C. taking very long reaction time in the reaction of the silylation of 5-substituted uracil with a silylating agent, e.g. hexamethyldisilazane. The methods (1), (2) and (3) with 2-chloro-, 2-acyloxy- or 2-alkoxytetrahydrofuran as the alkylating agent at the $N_1$-position of the uracil compound are also disadvantaged by the step of the preparation of the 2-substituted tetrahydrofurans starting with 2,3-dihydrofuran as well as by the thermal instability of these 2-substituted tetrahydrofurans, especially 2-chlorotetrahydrofuran, even at room temperature.

In addition, the above described prior art methods, which take disadvantageously long reaction time generally, also suffer from the disadvantages due to the more or less inevitable formation of by-products such as 1,3-bis(2-tetrahydrofuryl)uracil derivatives along with the formation of the objective $N_1$-(2-tetrahydrofuryl)uracil derivatives necessitating additional process for the isolation and purification of the objective product resulting in undesirable lowering in the quality and yield of the product.

Recently an alternative method has been proposed in which an uracil compound substituted at the 5-position is directly reacted with 2,3-dihydrofuran in the presence of an accelerator for the reaction such as amine salts, combinations of an organic base and a metal halide or amphoteric compounds (see, for example, Japanese Patent Disclosure Sho. No. 52-89680 and German OLS Nos. 2,653,398 and 2,657,709). This method is also not free from the above described problems in the prior art methods though with somewhat improved yield of the product. In particular, the reaction of this method must be performed at an elevated temperature of 80° to 200° C. by use of an autoclave.

SUMMARY OF THE INVENTION

It is therefore an object of the present invention to provide a novel and advantageous method for the preparation of 5-substituted or unsubstituted $N_1$-(2-tetrahydrofuryl)uracil derivatives free from the above described problems in the prior art methods carried out under mild reaction conditions taking relatively short reaction time.

It is another object of the present invention to provide a method for the preparation of the above compounds in a high yield without the formation of undesirable by-products.

In the method of the present invention, the objective uracil derivatives represented by the general formula,

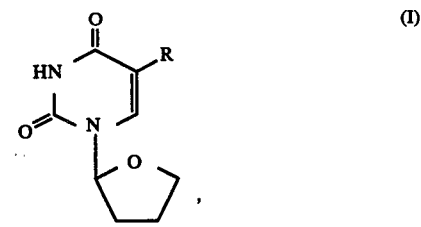

(I)

where R is a hydrogen atom, a halogen atom, an alkyl group, e.g. methyl group, or a trihalogenoalkyl group, e.g. trifluoromethyl group, is synthesized by the reaction of an uracil compound represented by the general formula

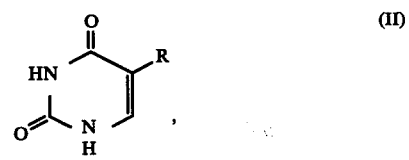

(II)

where the symbol R has the same meaning as defined above, with 2,3-dihydrofuran in the presence of a catalytic amount of an organic amine and a chlorine-containing silane compound represented by the general formula

(III)

where $R^1$ is a hydrogen atom, a hydrocarbyl group or a hydrocarbyloxy group, $R^2$ and $R^3$ are each a halogen atom, a hydrocarbyl group or a hydrocarbyloxy group, and X is a halogen atom.

The method of the present invention is especially suitable for the preparation of $N_1$-(2-tetrahydrofuryl)-5-fluorouracil.

DETAILED DESCRIPTION OF THE PREFERRED EMBODIMENTS

In the method of the invention, one of the starting reactants is uracil or a 5-substituted uracil compound represented by the above general formula (II) substituted at the 5-position with a halogen atom, an alkyl group or a trihalogenoalkyl group. The halogen atoms as the substituent at the 5-position is a fluorine, chlorine, bromine or iodine atom but it is natural that the halogen atom is a fluorine atom when $N_1$-(2-tetrahydrofuryl)-5-fluorouracil is the intended product. The alkyl group as the substituent at the 5-position is preferably a lower alkyl group such as methyl group. The trihalogenoalkyl group as the substituent at the 5-position is preferably trifluoromethyl group.

The halogen-containing organosilane compound or silyl halide compound represented by the general formula (III) above must have at least one halogen atom, preferably chlorine atom, directly bonded to the silicon atom and can have 2 or 3 halogen atoms directly bonded to the silicon atom. The remainder of the substituents other than the hydrogen atoms bonded to the silicon atom is hydrocarbyl groups exemplified by alkyl groups, e.g. methyl, ethyl and propyl groups, alkenyl groups, e.g. vinyl and allyl groups and aryl groups, e.g. phenyl groups, or hydrocarbyloxy groups exemplified by alkoxy groups, e.g. methoxy, ethoxy, propoxy, and butoxy groups, alkenyloxy groups, e.g. isopropenyloxy group, and aryloxy groups, e.g. phenoxy group. The examples of the halogen-containing silane compounds suitable for the purpose are trimethylchlorosilane, methyldimethoxychlorosilane, trimethoxychlorosilane, triethoxychlorosilane, methyldichlorosilane, methylphenyldichlorosilane, methylvinyldichlorosilane, diphenyldichlorosilane, dimethoxydichlorosilane, diethoxydichlorosilane, dibutoxydichlorosilane, dimethyldichlorosilane, trichlorosilane, methyltrichlorosilane, phenyltrichlorosilane, vinyltrichlorosilane and the like. Among the above named halogen-containing silane compounds, the most preferred is dimethyldichlorosilane by the reasons of higher yields of the objective compounds.

The organic amines used in a catalytic amount in the method of the invention include primary amines such as propylamine, isopropylamine, n-butylamine, tert-butylamine, aniline, benzylamine and the like, secondary amines such as diethylamine, dipropylamine, dibutylamine, piperidine, morpholine and the like, and tertiary amines such as triethylamine, N-methylpiperidine, N-methylmorpholine, N,N-dimethylaniline, N,N-diethylaniline, pyridine, quinoline and the like. Among the above amines, tertiary amines, especially triethylamine, are preferred although the preference of the amine largely depends on the combination of the other reactants or reagents.

The molar ratios of the reactants or reagents above described are preferably in the ranges of from 1.0 to 2.0 moles or, more preferably, 1.0 to 1.5 moles of 2,3-dihydrofuran, 0.05 to 0.2 mole or, more preferably, 0.05 to 0.1 mole of the organic amine compound and 2.0 to 2.5 moles of the halogen-containing silane compound of the formula (III) per mole of the uracil compound of the formula (II) though not so limitative especially for the amine compound and the silane compound.

The reaction of the inventive method proceeds rapidly even at low temperatures and usually performed at room temperature although it is optional to heat the reaction mixture at a slightly elevated temperature of up to about 40° C. or so.

It is recommendable to carry out the reaction of the inventive method by diluting the reaction mixture with 5 to 10 times by weight of an organic solvent. The organic solvent used for the purpose is preferably a polar, non-protonic solvent such as acetonitrile, dioxane and the like or a mixture thereof. Among them acetonitrile is the most preferred by the reasons of higher reaction rates.

The reaction time necessary for completion of the reaction depends on the solvent and the reaction temperature but 30 minutes to 2 hours of the reaction time is usually sufficient for the completion of the reaction as determined by periodical sampling of the reaction mixture under reaction followed by the analysis by thin-layer chromatography. In particular, the reaction proceeds rapidly in acetonitrile taking about 30 to 40 minutes for completion. This rapidness of the reaction is the most surprising result of the invention in comparison with the rather lengthy reaction time in the prior art methods.

A general procedure for carrying out the method of the present invention is as follows.

Into a mixture of the uracil compound and 2,3-dihydrofuran in the solvent, e.g. acetonitrile, containing a catalytic amount of the organic amine and kept at room temperature under agitation in a dry atmosphere, is added the halogen-containing silane compound and the reaction mixture is further agitated for a time, say, 1 hour or less, at room temperature or, if necessary, at a temperature slightly elevated. After the end of the above reaction time, the reaction mixture is admixed with chloroform, stirred, and poured into a chilled aqueous alkaline solution of an alkali hydroxide, e.g. sodium hydroxide, or alkali carbonate, e.g. sodium carbonate, with agitation followed by neutralization with diluted hydrochloric acid to weak acidity. The organic solution in the lower layer separated by standing is taken and the aqueous solution in the upper layer is repeatedly extracted with small portions of chloroform to recover any product contained in the aqueous solution. The chloroform solution and the chloroform extracts are dehydrated altogether and, optionally after treatment with charcoal, the solvents are removed by distillation under reduced pressure leaving a residue which is subsequently admixed with isopropyl alcohol to wash out the remaining silane compound. The mixture is agitated well for about 30 minutes and the dispersed solid matter is allowed to settle, filtered and washed with a small portion of cold isopropyl alcohol. By this treatment with isopropyl alcohol, the above residue colored in brown becomes decolorized. The thus obtained product is identified by measuring the melting point and the single spot appearing in the thin-layer chromatograph gives an evidence of the purity of the product. The product is further confirmed by NMR, IR and UV absorption spectral analyses to be compared with the data obtained for the corresponding standard sample indicating the absence of the undesirable by-products as the impurities.

As is understood from the description above given, the inventive method is very suitable for industrialization owing to the advantages of the rapidness of the reaction, the simplicity of the procedures, the high purity of the obtained products, the use of a simple reaction apparatus without the necessity of any heating or cooling means and the relative inexpensiveness and stability of 2,3-dihydrofuran as the reactant in comparison with the 2-substituted tetrahydrofurans used in the prior art methods.

Following are the examples to illustrate the method of the present invention in further detail but not to limit the scope of the invention.

EXAMPLE 1

Into a mixture of 60 g of 5-fluorouracil and 50 g of 2,3-dihydrofuran in 480 ml of acetonitrile was slowly added 5.2 g. of triethylamine and then 127.7 g of dimethyldichlorosilane was added as a portion at 15° C. followed by the reaction at 30°–35° C. for 2 hours. After the end of the above reaction time, the reaction mixture was cooled to room temperature and admixed with 480 ml of chloroform.

The reaction mixture was poured into a chilled aqueous solution of sodium hydroxide in another vessel under agitation and then acidified with 6 N hydrochloric acid to a pH value of 4.4–4.5. The aqueous solution in the upper layer separated by standing was taken and twice extracted with small portions of chloroform. Thus obtained organic solution was, after dehydration with anhydrous magnesium sulfate, subjected to distillation under reduced pressure to leave light brown solid as a residue. This residue was treated with a small amount of chilled isopropyl alcohol with agitation and the insoluble crystals were taken by filtration. This crystalline material was washed with cold isopropyl alcohol repeatedly, air-dried and further dried by heating to give 78.9 g of white crystalline material which was identified as the objective $N_1$-(2-tetrahydrofuryl)-5-fluorouracil having a melting point of 168°–169° C. and giving a single spot by thin-layer chromatography. The yield was 85.5% of the theoretical.

EXAMPLE 2

Into a mixture of 5.0 g of 5-fluorouracil, 4.1 g of 2,3-dihydrofuran and 0.3 g of pyridine in 40 ml of acetonitrile kept at 15° C. was added 10.4 g dimethyldichlorosilane as a portion and the reaction took place for about 30 minutes at 20°–26° C. The procedure for the treatment of the reaction mixture after the above reaction time was analogous to that in Example 1 to give 5.8 g of crystalline product of $N_1$-(2-tetrahydrofuryl)-5-fluorouracil having a melting point of 168.9° C. The yield was 75.4% of the theoretical.

EXAMPLE 3

The same procedure as in Example 2 was repeated except that 0.33 g of piperidine was used in place of 0.3 g of pyridine to give 6.1 g of crystalline product of $N_1$-(2-tetrahydrofuryl)-5-fluorouracil having a melting point of 168.5° C. The yield was 79.3% of the theoretical.

EXAMPLE 4

The same procedure as in Example 2 was repeated except that 0.41 g of benzylamine was used in place of 0.3 g of pyridine to give 5.3 g of crystalline product of $N_1$-(2-tetrahydrofuryl)-5-fluorouracil having a melting point of 168° C. The yield was 68.9% of the theoretical.

EXAMPLE 5

Into a mixture of 5.0 g of uracil, 4.7 g of 2,3-dihydrofuran and 0.45 g of triethylamine in 40 ml of acetonitrile kept at 15° C. was added 12.09 g of dimethyldichlorosilane as a portion and the reaction was conducted for about 60 minutes. The treatment of the reaction mixture after the above reaction time was the same as in Example 1 to give 3.6 g of a crystalline product of $N_1$-(2-tetrahydrofuryl)uracil having a melting point of 104° C. with 44.4% yield of the theoretical. The aqueous solution of this compound had a maximum absorption of ultraviolet light at a wavelength of 256 nm.

EXAMPLE 6

Into a mixture of 5.0 g of 5-fluorouracil, 4.1 g of 2,3-dihydrofuran and 0.45 g of triethylamine in 40 ml of acetonitrile kept at 15° C. was added a chlorosilane compound as indicated in Table I below in an amount of 2.1 times of the 5-fluorouracil by moles.

The yields of the objective $N_1$-(2-tetrahydrofuryl)-5-fluorouracil obtained by the reaction time as indicated in the table are summarized in the table.

As is clear from the results given in the table, it is a conclusion that methyldichlorosilane, methylphenyldichlorosilane, or methylvinyldichlorosilane as a chlorine-containing silane compound can give considerably high yields of $N_1$-(2-tetrahydrofuryl)-5-fluorouracil though with the highest preference of dimethyldichlorosilane as the silane compound.

Table I

| Experiment No. | Chlorine-containing silane compound | Reaction time, minutes | Yield Grams | % of the theoretical |
|---|---|---|---|---|
| 1 | Methyldichlorosilane | 60 | 6.1 | 79.3 |
| 2 | Methylphenyldichlorosilane | 52 | 5.5 | 71.5 |
| 3 | Methylvinyldichlorosilane | 42 | 6.2 | 80.6 |
| 4 | Diphenyldichlorosilane | 113 | 4.2 | 54.6 |
| 5 | Trichlorosilane | 46 | 2.7 | 35.0 |
| 6 | Methyltrichlorosilane | 79 | 3.7 | 48.1 |
| 7 | Vinyltrichlorosilane | 40 | 4.1 | 53.3 |
| 8 | Phenyltrichlorosilane | 60 | 4.9 | 63.7 |

EXAMPLE 7

Into a mixture of 5.0 g of 5-fluorouracil, 4.1 g of 2,3-dihydrofuran and 0.45 g of triethylamine in 40 ml of acetonitrile kept at 15° C. was added 9.2 g of trimethylchlorosilane as a portion to have the reaction take place followed by the same procedure for the treatment of the reaction mixture after the reaction as in Example 1 to give 2.8 g of a crystalline product of $N_1$-(2-tetrahydrofuryl)-5-fluorouracil having a melting point of 167.6° C. The yield was 36.4% of the theoretical.

EXAMPLE 8

Into a mixture of 5.0 g of 5-methyluracil, 4.2 g of 2,3-dihydrofuran and 0.4 g of triethylamine in 40 ml of acetonitrile kept at 15° C. under agitation was added 10.7 g of dimethyldichlorosilane as a portion and the reaction was continued for about 1 hour with agitation. The treatment procedure after completion of the reaction was much the same as in Example 1 to give 6.5 g of a crystalline product of $N_1$-(2-tetrahydrofuryl)-5-methyluracil having a melting point of 183.5° C. The yield was 83.6% of the theoretical.

EXAMPLE 9

Into a mixture of 5.0 g of 5-trifluoromethyluracil, 2.9 g of 2,3-dihydrofuran and 0.3 g of triethylamine in 40 ml of dioxane kept at 15° C. under agitation was added 7.5 g of dimethyldichlorosilane as a portion and the reaction was continued for about 2 hours with agitation. The treatment procedure after completion of the reaction was much the same as in Example 1 to give 5.0 g of a crystalline product of $N_1$-(2-tetrahydrofuryl)-5-trifluoromethyluracil having a melting point of 208° C. The yield was 72.0% of the theoretical.

What is claimed is:

1. A method for the preparation of uracil represented by the general formula

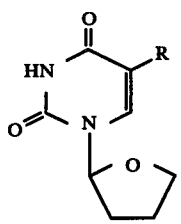

where R is a hydrogen atom, a halogen atom, an alkyl group or a trihalogenoalkyl group, which comprises reacting an uracil compound represented by the general formula

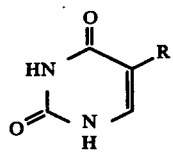

where R has the same meaning as defined above, with 2,3-dihydrofuran in the presence of a chlorine-containing silane compound represented by the general formula

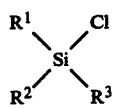

where $R^1$ is a hydrogen atom, a hydrocarbyl group or a hydrocarbyloxy group, and $R^2$ and $R^3$ are each a hydrocarbyl group, a hydrocarbyloxy group or a chlorine atom, and about 0.05 to 0.2 mole of an organic amine compound per mole of the uracil compound.

2. The method as claimed in claim 1 wherein the alkyl group represented by the symbol R is a methyl group.

3. The method as claimed in claim 1 wherein the trihalogenoalkyl group represented by the symbol R is a trifluoromethyl group.

4. The method as claimed in claim 1 wherein the chlorine-containing silane compound is dimethyldichlorosilane.

5. The method as claimed in claim 1 wherein the organic amine compound is a tertiary amine.

6. The method as claimed in claim 5 wherein the tertiary amine is triethylamine.

7. The method as claimed in claim 1 wherein the amount of the 2,3-dihydrofuran is in the range from 1.0 to 2.0 moles per mole of the uracil compound.

8. The method as claimed in claim 1 wherein the reaction of the uracil compound and the 2,3-dihydrofuran is carried out at a temperature in the range from room temperature to 40° C.

9. The method as claimed in claim 1 wherein the reaction of the uracil compound and the 2,3-dihydrofuran is carried out in a polar, non-protonic organic solvent.

10. The method as claimed in claim 9 wherein the polar, non-protonic organic solvent is acetonitrile.

11. A method for the preparation of $N_1$-(2-tetrahydrofuryl)-5-fluorouracil which comprises reacting 5-fluorouracil with 2,3-dihydrofuran in the presence of a chlorine-containing silane compound represented by the general formula

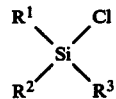

where $R^1$ is a hydrogen atom, a hydrocarbyl group or a hydrocarbyloxy group, and $R^2$ and $R^3$ are each a hydrocarbyl group, a hydrocarbyloxy group or a chlorine atom, and about 0.05 to 0.2 mole of an organic amine compound per mole of the uracil compound.

12. The method as claimed in claim 11 wherein the chlorine-containing silane compound is dimethyldichlorosilane and the reaction is carried out in acetonitrile.

* * * * *